(12) United States Patent
Higuchi et al.

(10) Patent No.: US 10,746,689 B2
(45) Date of Patent: Aug. 18, 2020

(54) SENSOR CONTROL APPARATUS

(71) Applicant: NGK Spark Plug Co., LTD., Nagoya (JP)

(72) Inventors: Yuzo Higuchi, Iwakura (JP); Satoru Abe, Ichinomiya (JP); Koji Ishibashi, Kasugai (JP)

(73) Assignee: NGK Spark Plug Co., LTD., Nagoya (JP)

( * ) Notice: Subject to any disclaimer, the term of this patent is extended or adjusted under 35 U.S.C. 154(b) by 202 days.

(21) Appl. No.: 15/899,184

(22) Filed: Feb. 19, 2018

(65) Prior Publication Data

US 2018/0306745 A1    Oct. 25, 2018

(30) Foreign Application Priority Data

Apr. 20, 2017   (JP) ................................. 2017-083786

(51) Int. Cl.
| | | |
|---|---|---|
| *G01N 27/406* | (2006.01) | |
| *G01N 27/419* | (2006.01) | |
| *G01N 27/407* | (2006.01) | |
| *G01N 27/417* | (2006.01) | |
| *G01N 33/00*  | (2006.01) | |

(Continued)

(52) U.S. Cl.
CPC ......... *G01N 27/4065* (2013.01); *G01N 27/12* (2013.01); *G01N 27/122* (2013.01); *G01N 27/4062* (2013.01); *G01N 27/4073* (2013.01); *G01N 27/414* (2013.01); *G01N 27/419* (2013.01); *G01N 27/4175* (2013.01); *G01N 33/004* (2013.01); *G01N 33/005* (2013.01)

(58) Field of Classification Search
CPC .... G01N 27/12; G01N 27/414; G01N 33/005; G01N 33/004; G01N 27/122
USPC ........................................................ 73/31.06
See application file for complete search history.

(56) References Cited

U.S. PATENT DOCUMENTS

| 6,567,738 B2 * | 5/2003 | Gopp ................... F02D 41/1441 123/691 |
|---|---|---|
| 2004/0026408 A1 * | 2/2004 | Morinaga ........... G01N 27/4067 219/497 |

(Continued)

FOREIGN PATENT DOCUMENTS

| JP | 2003090821 | * 3/2003 | ............. F02D 41/22 |
|---|---|---|---|
| JP | 2008-70194 A | 3/2008 | |

*Primary Examiner* — Clayton E. LaBalle
*Assistant Examiner* — Kevin C Butler
(74) *Attorney, Agent, or Firm* — Leason Ellis LLP

(57) ABSTRACT

A sensor element drive circuit is a circuit including a plurality of semiconductor elements formed on a semiconductor substrate for realizing a current control function and a switching function. The current control function is a function of controlling the current flowing between electrodes such that the potential difference between electrodes becomes constant. The switching function is a function for switching between a connected state in which the electrodes are electrically connected to a sensor control apparatus and a cut-off state in which electrical continuity therebetween is broken. When one of an Ip+ terminal, a COM terminal, and a Vs+ terminal is determined to have an anomalous potential, the sensor control apparatus causes the sensor element drive circuit to perform switching from the connected state to the cut-off state, and connects the semiconductor substrate to a negative voltage lower than a ground potential applied to the sensor element drive circuit.

7 Claims, 4 Drawing Sheets

(51) Int. Cl.
*G01N 27/414* (2006.01)
*G01N 27/12* (2006.01)

(56) References Cited

U.S. PATENT DOCUMENTS

| | | | | |
|---|---|---|---|---|
| 2005/0029098 A1* | 2/2005 | Aoki | ............. | G01N 27/4065 204/406 |
| 2005/0288847 A1* | 12/2005 | Inoue | ............. | G01N 27/4175 701/114 |
| 2006/0157348 A1* | 7/2006 | Inoue | ............. | F02D 41/1494 204/401 |
| 2008/0060941 A1* | 3/2008 | Ieda | ............. | G01N 27/4065 204/431 |

* cited by examiner

SENSOR CONTROL APPARATUS

This application claims the benefit of Japanese Patent Application No. 2017-083786, filed Apr. 20, 2017, which is incorporated herein by reference in its entirety.

FIELD OF THE INVENTION

The present disclosure relates to a sensor control apparatus for controlling a gas sensor.

BACKGROUND OF THE INVENTION

As disclosed in Japanese Patent Application Laid-Open (kokai) No. 2008-70194, there has been known a technique of electrically cutting off (breaking) the continuity between a gas sensor and a sensor control apparatus, thereby preventing flow of current into the gas sensor, when a wiring anomaly occurs and some of wiring lines electrically connected to the gas sensor are shorted to a power supply potential or a ground potential. The technique can reduce the possibility of an excessive current flowing into the gas sensor and breaking the gas sensor.

Problem to be Solved by the Invention

However, there has been a problem that even when the continuity between the gas sensor and the sensor control apparatus is cut off, in some cases, an excessive current flows into the gas sensor and the gas sensor breaks.

An object of the present disclosure is to prevent breakage of the gas sensor.

SUMMARY OF THE INVENTION

Means for Solving the Problem

One mode of the present disclosure is a control system comprising a gas sensor for detecting the concentration of a particular gas contained in a target gas and a sensor control apparatus which controls the gas sensor.

The gas sensor includes an electromotive force cell and a pump cell. The electromotive force cell has a first solid electrolyte member and paired first electrodes formed on the first solid electrolyte member, and is configured to generate electromotive force between the paired first electrodes in accordance with a difference in concentration of the particular gas therebetween. The pump cell has a second solid electrolyte member and paired second electrodes formed on the second solid electrolyte member, and is configured to pump the particular gas between the paired second electrodes.

The sensor control apparatus of the present disclosure comprises a control circuit, an anomaly determination section, a state switching section, and a potential connection section.

The control circuit has a plurality of semiconductor elements formed on a semiconductor substrate, the semiconductor elements being provided for a current control function and a switching function.

The current control function is a function of controlling current flowing between the paired second electrodes such that a constant potential difference is produced between the paired first electrodes.

The switching function is a function for switching between a connected state in which the paired first electrodes and the paired second electrodes are electrically connected to the sensor control apparatus and a cut-off state in which electrical continuity between the sensor control apparatus and the paired first electrodes and electrical continuity between the sensor control apparatus and the paired second electrodes are cut off.

The anomaly determination section determines, on the basis of an anomaly determination condition set in advance, whether or not at least one of a plurality of connection points for connecting the control circuit to the paired first electrodes and the paired second electrodes of the gas sensor has an anomalous potential.

The state switching section causes the control circuit to perform switching from the connected state to the cut-off state, when the anomaly determination section determines that the at least one connection point has an anomalous potential. The potential connection section connects the semiconductor substrate to an anomaly-time potential lower than a reference potential applied to the control circuit, when the anomaly determination section determines that the at least one connection point has an anomalous potential.

In the sensor control apparatus of the present disclosure configured as described above, parasitic diodes are formed between the semiconductor substrate and the semiconductor elements formed on the semiconductor substrate. The parasitic diodes have characteristics of limiting the current flowing from the semiconductor elements to the semiconductor substrate. The parasitic diodes also have characteristics of allowing the current flowing from the semiconductor substrate to the semiconductor elements to flow more easily as compared with the current flowing from the semiconductor elements to the semiconductor substrate.

In the sensor control apparatus of the present disclosure, leak currents flow from the semiconductor elements to the semiconductor substrate through the parasitic diodes. The magnitudes of the leak currents increase as the temperature of the control circuit increases. If the leak current from a certain semiconductor element reaches the semiconductor substrate through the corresponding parasitic diode, the leak current flows toward another semiconductor element whose potential is set to the reference potential among the plurality of semiconductor elements.

Therefore, in the case where there exists a path of leak current which extends from one of the connection points, passes through the corresponding semiconductor element, reaches the semiconductor substrate, and extends from the semiconductor substrate toward another semiconductor element whose potential is the reference potential, a current corresponding to the magnitude of the leak current flows to the gas sensor even in the above-described cut-off state.

In view of this, in the case where one of the connection points has an anomalous potential, the sensor control apparatus of the present disclosure connects the semiconductor substrate to an anomaly-time potential which is lower than the reference potential applied to the control circuit.

Therefore, even when a leak current from a certain semiconductor element reaches the semiconductor substrate through the corresponding parasitic diode, the sensor control apparatus of the present disclosure can prevent the leak current from further flowing from the semiconductor substrate toward another semiconductor element whose potential is the reference potential.

Thus, the sensor control apparatus of the present disclosure can prevent a current corresponding to the magnitude of the leak current from flowing into the gas sensor, which flow would otherwise occur even in the above-described cut-off state. As a result, the sensor control apparatus can prevent breakage of the gas sensor.

In the one mode of the present disclosure, the potential connection section may include a negative charge pump for generating a negative voltage, and when the anomaly determination section determines that the at least one connection point has an anomalous potential, the potential connection section may activate the negative charge pump and use the negative voltage generated by the negative charge pump as the anomaly-time potential.

Since the sensor control apparatus of the present disclosure configured as described above applies a negative voltage to the semiconductor substrate as the anomaly-time potential, the reference potential applied to the control circuit can be made equal to or higher than 0 V. In general, the reference potential of the control circuit is 0 V. Therefore, the sensor control apparatus of the present disclosure can prevent breakage of the gas sensor without changing the reference potential applied to the control circuit.

In the one mode of the present disclosure, the gas sensor may be configured such that when constant current flows between the paired first electrodes of the electromotive force cell, the concentration of oxygen around one of the paired first electrodes becomes constant.

The sensor control apparatus of the present disclosure configured as described above can prevent a current corresponding to the magnitude of the leak current from flowing into the electromotive force cell, which flow would otherwise occur even in the above-described cut-off state. As a result, the sensor control apparatus can prevent blackening of the electromotive force cell. Blackening is a phenomenon in which the external color of the solid electrolyte member changes and metallic oxide constituting the solid electrolyte member is reduced and oxygen is removed, whereby the crystalline structure is disordered.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embodiment of the present disclosure will be described with reference to the drawings.

A control system 1 of the present embodiment executes various control processes for controlling the operation state of an internal combustion engine, and executes, as one of them, a process of detecting the concentration of a particular gas contained in exhaust gas. In the present embodiment, the particular gas is oxygen.

Figure 1:
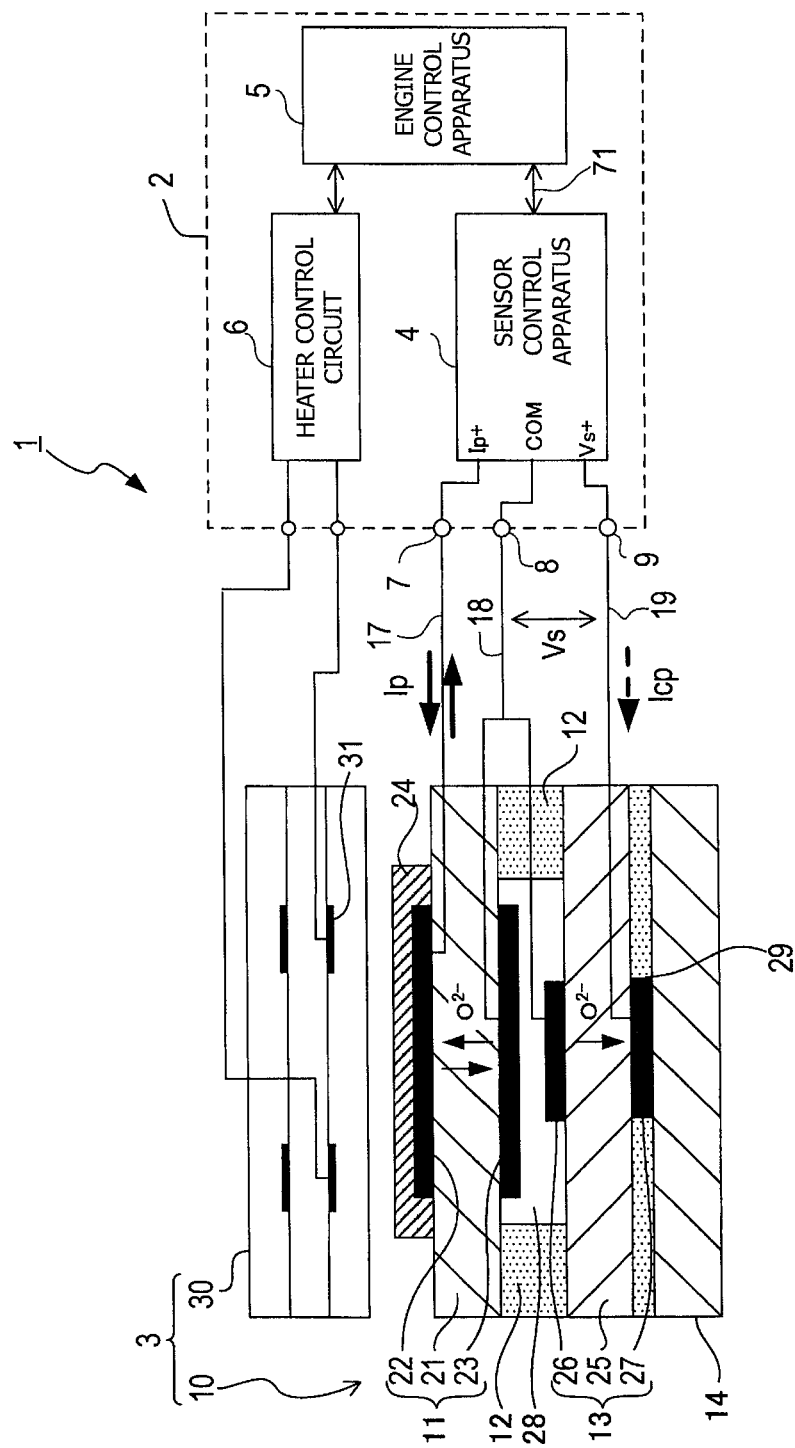
FIG. 1 is a diagram schematically showing the configuration of a control system 1.

As shown in FIG. 1, the control system 1 includes an electronic control unit 2 and a gas sensor 3. The electronic control unit 2 includes a sensor control apparatus 4, an engine control apparatus 5, and a heater control circuit 6.

The gas sensor 3 includes a sensor element 10 for detecting the oxygen concentration in exhaust gas for a wide range and a heater 30 for maintaining the sensor element 10 at an operating temperature.

The sensor element 10 includes an oxygen pump cell 11, porous diffusion layers 12, an oxygen concentration detection cell 13, and a reinforcing plate 14.

The oxygen pump cell 11 has an oxygen-ion conductive solid electrolyte member 21 formed of partially stabilized zirconia and having a plate-like shape, and pump electrodes 22 and 23 provided on the front and back surfaces of the oxygen-ion conductive solid electrolyte member 21 and formed mainly of platinum. The pump electrode 22 is electrically connected to a connection terminal 7 of the electronic control unit 2 through a wiring line 17. The pump electrode 23 is electrically connected to a connection terminal 8 of the electronic control unit 2 through a wiring line 18. The pump electrode 22 is covered with a porous protection layer 24 which protects the pump electrode 22 from poisoning substances or the like.

The oxygen concentration detection cell 13 has an oxygen-ion conductive solid electrolyte member 25 formed of partially stabilized zirconia and having a plate-like shape, and detection electrodes 26 and 27 provided on the front and back surfaces of the oxygen-ion conductive solid electrolyte member 25 and formed mainly of platinum. The detection electrode 26 is electrically connected to the connection terminal 8 of the electronic control unit 2 through the wiring line 18 and is electrically connected to the pump electrode 23. The detection electrode 27 is electrically connected to a connection terminal 9 of the electronic control unit 2 through a wiring line 19.

An unillustrated insulating layer formed mainly of an insulating material (e.g., alumina) is provided between the oxygen pump cell 11 and the oxygen concentration detection cell 13 so as to electrically insulate the two cells 11 and 13 from each other. The porous diffusion layers 12 are provided in portions of the insulating layer. Notably, the porous diffusion layers 12 are formed mainly of an insulating material (e.g., alumina) to be porous for limiting the diffusion rate of a gas under measurement introduced into the sensor element 10.

A hollow measurement chamber 28 surrounded by the porous diffusion layers 12 and the unillustrated insulating layer is formed between the oxygen pump cell 11 and the oxygen concentration detection cell 13. Namely, the measurement chamber 28 communicates with a measurement gas atmosphere through the porous diffusion layers 12. The pump electrode 23 and the detection electrode 26 are disposed in the measurement chamber 28.

The reinforcing plate 14 is disposed on a surface of the oxygen concentration detection cell 13 on the side opposite a surface thereof facing the measurement chamber 28 such that the reinforcing plate 14 is in close contact with the former surface while sandwiching the detection electrode 27. As a result, the reinforcing plate 14 increases the overall strength of the sensor element 10. Notably, the reinforcing plate 14 has a size approximately the same as those of the solid electrolyte members 21 and 25 of the oxygen pump cell 11 and the oxygen concentration detection cell 13 and is formed of a material whose main component is ceramic.

The detection electrode 27 of the oxygen concentration detection cell 13 is isolated from the outside by the reinforcing plate 14, and a reference oxygen chamber 29 which is a closed space is formed between the oxygen concentration detection cell 13 and the reinforcing plate 14 around the detection electrode 27.

In the sensor element 10 configured as described above, a small constant current Icp is caused to flow from the detection electrode 27 of the oxygen concentration detection cell 13 toward the detection electrode 26 so as to pump oxygen from the measurement chamber 28 toward the detection electrode 27. As a result, oxygen of an approximately constant concentration is accumulated in the reference oxygen chamber 29 formed around the detection electrode 27. The oxygen of an approximately constant concentration accumulated in the reference oxygen chamber 29 serves as a reference oxygen concentration when the oxygen concentration in the gas under measurement is detected by the sensor element 10. Therefore, the detection electrode 27 is also called a self-generating reference electrode.

The heater 30 is formed to have a flat-plate-like shape and is disposed to face the oxygen pump cell 11 of the sensor element 10. The heater 30 is formed of a material whose main component is alumina, and includes a heater wire 31 formed of a material whose main component is platinum. The heater 30 is controlled by electric power supplied from the heater control circuit 6 such that the temperature of the sensor element 10 becomes an activation temperature (e.g., 550 to 900° C.). Opposite ends of the heater wire 31 are electrically connected to the heater control circuit 6.

Notably, when the sensor element 10 becomes active as a result of heating by the heater 30, the gas sensor 3 enters a gas detectable state.

The sensor control apparatus 4 has an Ip+ terminal, a COM terminal, and a Vs+ terminal. The Ip+ terminal, the COM terminal, and the Vs+ terminal are electrically connected to the connection terminal 7, the connection terminal 8, and the connection terminal 9, respectively, of the electronic control unit 2. Therefore, the pump electrode 22 of the sensor element 10 is electrically connected to the Ip+ terminal of the sensor control apparatus 4 through the connection terminal 7. The pump electrode 23 and the detection electrode 26 of the sensor element 10 is electrically connected to the COM terminal of the sensor control apparatus 4 through the connection terminal 8. The detection electrode 27 of the sensor element 10 is electrically connected to the Vs+ terminal of the sensor control apparatus 4 through the connection terminal 9.

In the sensor element 10, oxygen contained in the gas under measurement diffuses into the measurement chamber 28 through the porous diffusion layers 12. The sensor element 10 has characteristics as follows. In a state in which an air-fuel mixture supplied to an internal combustion engine is maintained at a stoichiometric air-fuel ratio, an electromotive force of 450 mV is produced in the oxygen concentration detection cell 13 due to the difference in oxygen concentration between the measurement chamber 28 and the reference oxygen chamber 29. Namely, a potential difference of 450 mV is produced between the detection electrode 26 and the detection electrode 27.

Notably, the oxygen concentration detection cell 13 has characteristics that it generates voltage corresponding to the difference in oxygen concentration between the detection electrode 26 and the detection electrode 27. The oxygen within the reference oxygen chamber 29 which the detection electrode 27 faces has an approximately constant concentration. Therefore, the oxygen concentration detection cell 13 generates, between the detection electrode 26 and the detection electrode 27, voltage corresponding to the oxygen concentration within the measurement chamber 28.

Incidentally, when the air-fuel ratio of the air-fuel mixture supplied to the internal combustion engine changes, the concentration of oxygen contained in exhaust gas changes, whereby the concentration of oxygen contained in the measurement chamber 28 of the sensor element 10 changes. In view of this, in the control system 1 of the present embodiment, the electronic control unit 2 controls the Ip current (pumping current) flowing through the oxygen pump cell 11 such that the potential difference between the detection electrode 26 and the detection electrode 27 is maintained at 450 mV. Namely, as a result of control of the Ip current such that the atmosphere within the measurement chamber 28 becomes the same as that in the case where the air-fuel ratio is the stoichiometric air-fuel ratio, pumping of oxygen is performed by the oxygen pump cell 11. Therefore, the oxygen concentration in the exhaust gas can be computed on the basis of the flow state of the Ip current (for example, flow direction, current cumulative value, etc.).

The oxygen pump cell 11 is configured such that, in accordance with the flow direction of current flowing between the pump electrode 22 and the pump electrode 23, the oxygen pump cell 11 can selectively perform the pumping out of oxygen from the measurement chamber 28 and the pumping of oxygen into the measurement chamber 28. Also, the oxygen pump cell 11 is configured such that it can adjust the oxygen pumping rate in accordance with the magnitude of the current flowing between the pump electrode 22 and the pump electrode 23.

Figure 2:
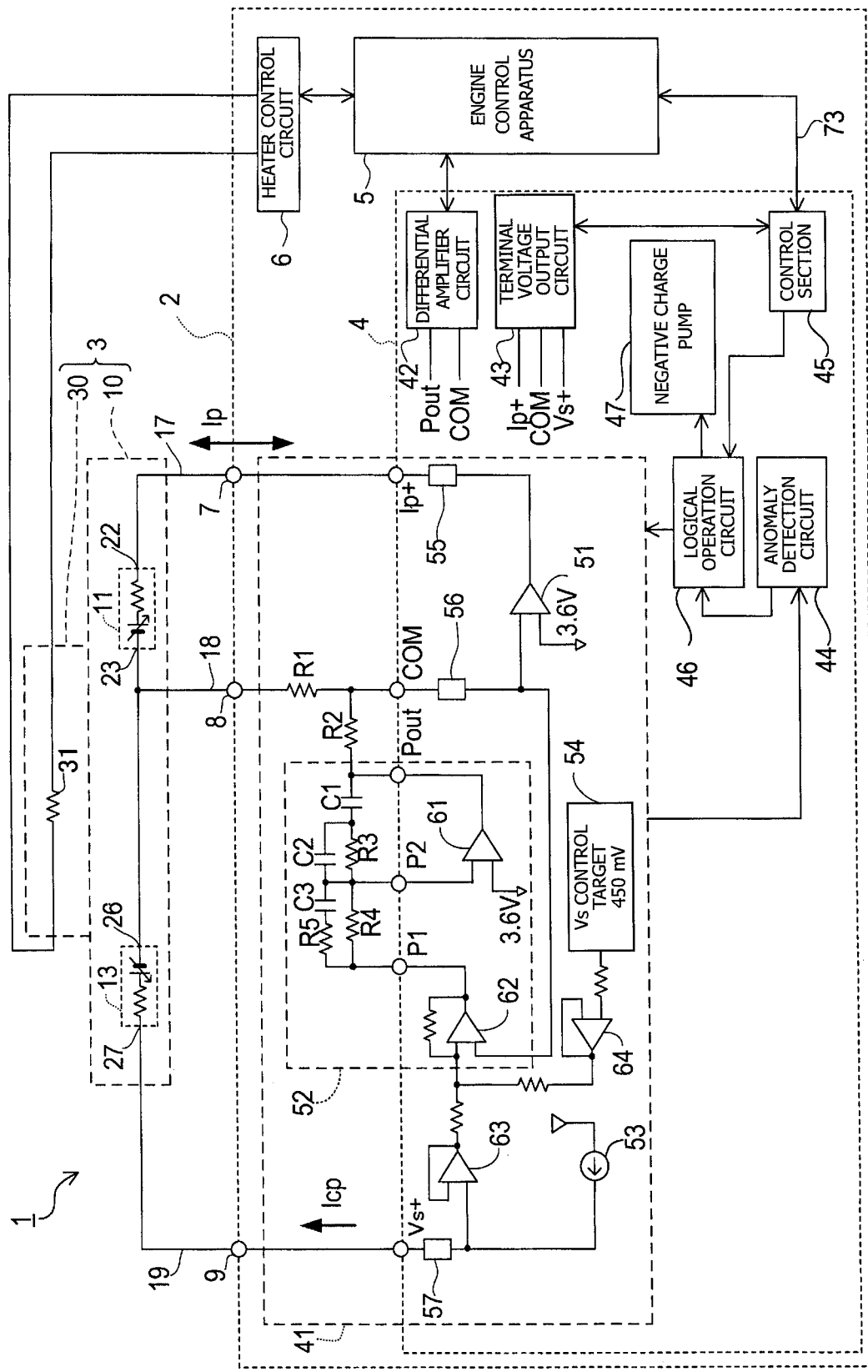
FIG. 2 is a circuit diagram schematically showing the configuration of an electronic control unit 2.

As shown in FIG. 2, the sensor control apparatus 4 includes a sensor element drive circuit 41, a differential amplifier circuit 42, a terminal voltage output circuit 43, an anomaly detection circuit 44, a control section 45, a logical operation circuit 46, and a negative charge pump 47. The sensor control apparatus 4 is realized by an application specific integrated circuit (i.e., ASIC). ASIC is an abbreviation of Application Specific IC.

The sensor element drive circuit 41 drives and controls the oxygen pump cell 11 and the oxygen concentration detection cell 13 of the sensor element 10.

The sensor element drive circuit 41 includes an operation amplifier 51 for supplying the Ip current for driving the oxygen pump cell 11, a PID control circuit 52 for improving the Ip current control characteristic, a constant current source 53 for supplying constant current Icp to the oxygen concentration detection cell 13, a constant voltage source 54 for supplying a control target voltage used for control of the Ip current, and semiconductor switches 55, 56, and 57.

The sensor element drive circuit 41 has the Ip+ terminal, the COM terminal, and the Vs+ terminal through which the sensor element drive circuit 41 is connected to the sensor element 10. The sensor element drive circuit 41 has a P1 terminal, a P2 terminal, and a Pout terminal to which elements for determining the characteristics of the PID control circuit 52 are externally attached.

The Ip+ terminal, the COM terminal, and the Vs+ terminal are electrically connected to the connection terminal 7, the connection terminal 8, and the connection terminal 9, respectively.

Of the two pump electrodes 22 and 23 of the oxygen pump cell 11, the pump electrode 22 is connected to the Ip+ terminal through the wiring line 17 and the connection terminal 7. The pump electrode 23 is connected, through the wiring line 18 and the connection terminal 8, to the COM terminal which provides a common reference voltage of the sensor element 10.

Of the two detection electrodes 26 and 27 of the oxygen concentration detection cell 13, the detection electrode 26 is connected to the COM terminal through the wiring line 18 and the connection terminal 8, and the detection electrode 27 is connected to the Vs+ terminal through the wiring line 19 and the connection terminal 9.

The PID control circuit 52 is connected to the inverting input terminal of the operation amplifier 51 through the semiconductor switch 56, the COM terminal, and a resistor element R2. A reference voltage of 3.6 V is applied to the non-inverting input terminal of the operation amplifier 51. The output terminal of the operation amplifier 51 is connected to the Ip+ terminal through the semiconductor switch 55. Namely, the operation amplifier 51 constitutes a portion of a negative feedback circuit which controls the current supplied to the sensor element 10; specifically, to the oxygen pump cell 11.

The PID control circuit 52 has a function of performing PID computation on the deviation ΔVs of the output voltage Vs of the oxygen concentration detection cell 13 from 450 mV (control target voltage), thereby improving the control characteristics of the above-mentioned negative feedback control. The PID control circuit 52 includes operation amplifiers 61 and 62, resistors R3, R4, and R5, and capacitors C1, C2, and C3. The resistors R3 to R5 and the capacitors C1 to C3 are attached to the P1 terminal and the P2 terminal so as to determine the control characteristics of the PID control circuit 52.

The input terminal of the PID control circuit 52 (namely, the inverting input terminal of the operation amplifier 62) is connected to the Vs+ terminal through an operation amplifier 63. As a result, the output voltage Vs of the oxygen concentration detection cell 13 is input to the PID control circuit 52. The output end of the PID control circuit 52 is connected to the Pout terminal. The Pout terminal is connected to the COM terminal through the resistor element R2 and is finally connected to the inverting input terminal of the operation amplifier 51.

The output of the constant voltage source 54 is input to the inverting input terminal of the operation amplifier 62 through an operation amplifier 64. The constant voltage source 54 is a circuit for supplying 450 mV, which is a voltage serving as a control target for control of the Ip current, to the PID control circuit 52 through the operation amplifier 62.

The constant current source 53 is connected to the Vs+ terminal through the semiconductor switch 57. The constant current source 53 is a circuit for supplying constant current Icp (for example, 17 μA) which is supplied to the oxygen concentration detection cell 13 so as to make the oxygen concentration around the detection electrode 27 of the oxygen concentration detection cell 13 (namely, the reference oxygen chamber 29) constant. The non-inverting input terminal of the operation amplifier 63 is connected to the Vs+ terminal through the semiconductor switch 57.

In the case where the gas under measurement is excessive in fuel supply (namely, rich), the oxygen concentration within the measurement chamber 28 becomes lower than that in the case of the stoichiometric air-fuel ratio, and the output voltage Vs of the oxygen concentration detection cell 13 becomes higher than 450 mV which is the control target voltage. Accordingly, the deviation ΔVs of the output voltage Vs from the control target voltage is produced, and the deviation ΔVs undergoes the PID computation performed by the PID control circuit 52 and is fed back by the operation amplifier 51. Therefore, the Ip current required for the oxygen pump cell 11 to pump oxygen into the measurement chamber 28 so as to compensate a shortage of oxygen flows through the oxygen pump cell 11.

Meanwhile, in the case where the gas under measurement is insufficient in fuel supply (namely, lean), the oxygen concentration within the measurement chamber 28 becomes higher than that in the case of the stoichiometric air-fuel ratio, and the output voltage Vs of the oxygen concentration detection cell 13 becomes lower than 450 mV which is the control target voltage. In the same manner as in the above-described case, the deviation ΔVs is fed back by the operation amplifier 51. Therefore, the Ip current required for the oxygen pump cell 11 to pump out the excessive portion of oxygen from the measurement chamber 28 flows through the oxygen pump cell 11.

As described above, the sensor element drive circuit 41 controls the Ip current supplied to the oxygen pump cell 11 such that the output voltage Vs of the oxygen concentration detection cell 13 becomes 450 mV.

The sensor element drive circuit 41 converts the Ip current flowing through the oxygen pump cell 11 to voltage through use of the resistor element R2 whose one end is connected to the COM terminal and whose other end is connected to the Pout terminal.

The differential amplifier circuit 42 amplifies the difference between the voltage at the COM terminal and the voltage at the Pout terminal and outputs the amplified difference to the engine control apparatus 5 as a gas detection signal.

The engine control apparatus 5 computes the oxygen concentration on the basis of the gas detection signal. The engine control apparatus 5 controls the operation state of the internal combustion engine by executing air-fuel ratio feedback control, etc. for the internal combustion engine on the basis of the oxygen concentration obtained as a result of the computation.

The terminal voltage output circuit 43 is a circuit for outputting the terminal voltages of the Ip+ terminal, the COM terminal, and the Vs+ terminal to the control section 45. Although connection lines are omitted in FIG. 2, the input terminals of the terminal voltage output circuit 43 are connected to the Ip+ terminal, the COM terminal, and the Vs+ terminal, respectively.

Figure 3:
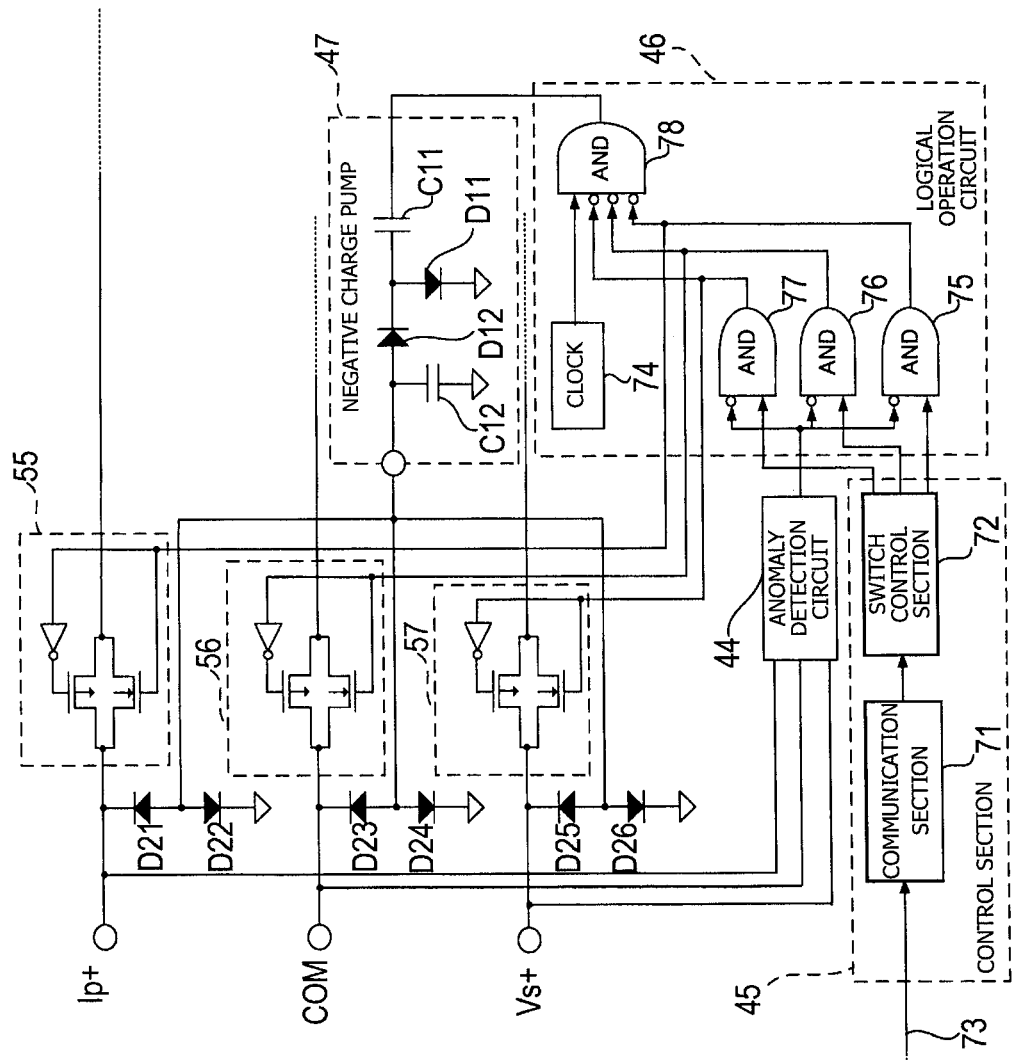
FIG. 3 is a circuit diagram showing the configurations of a control section 45, a logical operation circuit 46, a negative charge pump 47, and semiconductor switches 55, 56, and 57.

The anomaly detection circuit 44 is a circuit for determining (detecting) whether or not any one of the Ip+ terminal, the COM terminal, and the Vs+ terminal is shorted to a power supply potential or a ground potential and for outputting an anomaly detection signal showing the results of the determination (detection). As shown in FIG. 3, the terminal voltages of the Ip+ terminal, the COM terminal, and the Vs+ terminal are input to the anomaly detection circuit 44. The anomaly detection circuit 44 is configured to output an anomaly detection signal of high level when any one of the input terminal voltages deviates from a normal voltage range. Also, the anomaly detection circuit 44 is configured to output an anomaly detection signal of low level when all the terminal voltages of the Ip+ terminal, the COM terminal, and the Vs+ terminal fall within the normal voltage range.

The control section 45 executes various control processes in the sensor control apparatus 4 and is mainly composed of a well known microcomputer which includes a CPU, a ROM, a RAM, an input port, an output port, and a bus line for connecting these components.

The various functions of the microcomputer are realized by a program which is stored in a non-transitory tangible recording medium and executed by the CPU. In this example, the ROM corresponds to the non-transitory tangible recording medium storing the program. Also, a method corresponding to the program is performed as a result of execution of this program. Notably, the control section 45 may include a single microcomputer or a plurality of microcomputers. Also, some or all of the functions of the microcomputer(s) may be realized by hardware; for example, by a single IC or a plurality of ICs.

The control section 45 includes a communication section 71 and a switch control section 72. The communication section 71 performs data communication with the engine control apparatus 5 through a transmission cable 73. When the communication section 71 receives a switch open/close instruction from the engine control apparatus 5, on the basis of the received switch open/close instruction, the switch control section 72 outputs first, second, and third switch control signals for bringing the semiconductor switches 55, 56, and 57 into an ON state or an OFF state. Specifically, in the case where the switch open/close instruction instructs the switch control section 72 to bring the semiconductor switch 55 into the ON state, the switch control section 72 outputs a high level signal as the first switch control signal. Meanwhile, in the case where the switch open/close instruction instructs the switch control section 72 to bring the semiconductor switch 55 into the OFF state, the switch control section 72 outputs a low level signal as the first switch control signal.

Similarly, in the case where the switch open/close instruction instructs the switch control section 72 to bring the semiconductor switch 56 into the ON state, the switch control section 72 outputs a high level signal as the second switch control signal. Meanwhile, in the case where the switch open/close instruction instructs the switch control section 72 to bring the semiconductor switch 56 into the OFF state, the switch control section 72 outputs a low level signal as the second switch control signal.

Further, in the case where the switch open/close instruction instructs the switch control section 72 to bring the semiconductor switch 57 into the ON state, the switch control section 72 outputs a high level signal as the third switch control signal. Meanwhile, in the case where the switch open/close instruction instructs the switch control section 72 to bring the semiconductor switch 57 into the OFF state, the switch control section 72 outputs a low level signal as the third switch control signal.

The logical operation circuit 46 includes a clock circuit 74 and AND circuits 75, 76, 77, and 78.

In order to operate the negative charge pump 47, the clock circuit 74 generates a clock signal at a frequency (for example, 8 MHz) set in advance, and outputs the clock signal to the AND circuit 78.

The AND circuits 75, 76, and 77 obtain the logical products between a signal obtained by inverting the voltage level of the anomaly detection signal output from the anomaly detection circuit 44 and the first, second, and third switch control signals output from the switch control section 72.

The AND circuit 78 obtains the logical product between the clock signal output from the clock circuit 74 and signals obtained by inverting the voltage levels of the signals output from the AND circuits 75, 76, and 77.

The negative charge pump 47 is a circuit for generating a negative voltage when the clock signal is input to the negative charge pump 47 through the AND circuit 78. The negative charge pump 47 includes capacitors C11 and C12 and diodes D11 and D12.

One end of the capacitor C11 is connected to the output terminal of the AND circuit 78, and the other end of the capacitor C11 is connected to the connection point between the diode D11 and the diode D12. The anode of the diode D11 is connected to the capacitor C11, and the cathode of the diode D11 is grounded. The anode of the diode D12 is connected to the output terminal of the negative charge pump 47, and the cathode of the diode D12 is connected to the connection point between the diode D11 and the capacitor C11. One end of the capacitor C12 is connected to the anode of the diode D12, and the other end of the capacitor C12 is grounded.

In the present embodiment, the negative charge pump 47 generates a negative voltage of, for example, −3 V.

Each of the semiconductor switches 55, 56, and 57 is formed by connecting an N-channel MOS FET and a P-channel MOS FET in parallel.

The gates of the N-channel MOS FETs of the semiconductor switches 55, 56, and 57 are respectively connected to the output terminals of the AND circuits 75, 76, and 77. The gates of the P-channel MOS FETs of the semiconductor switches 55, 56, and 57 are respectively connected to the output terminals of the AND circuits 75, 76, and 77 through respective logical inversion circuits. As a result, the semiconductor switch 55 (56, 57) enters the ON state when a signal of high level is output from the AND circuit 75 (76, 77) and enters the OFF state when a signal of low level is output from the AND circuit 75 (76, 77).

Notably, parasitic diodes are formed on a semiconductor substrate on which the sensor control apparatus 4 realized by an ASIC is formed. As a results, parasitic diodes D21, D22, D23, D24, D25, and D26 are formed in the sensor element drive circuit 41.

The cathodes of the parasitic diodes D21, D23, and D25 are connected to the Ip+ terminal, the COM terminal, and the Vs+ terminal, respectively, The anodes of the parasitic diodes D21 to D26 are connected to the output terminal of the negative charge pump 47.

The cathodes of the parasitic diodes D22, D24, and D26 are grounded. Therefore, in a state in which the clock signal is not input to the negative charge pump 47, the potential of the above-mentioned semiconductor substrate becomes substantially equal to the ground potential due to presence of the parasitic diodes D22, D24, and D26.

Figure 4:
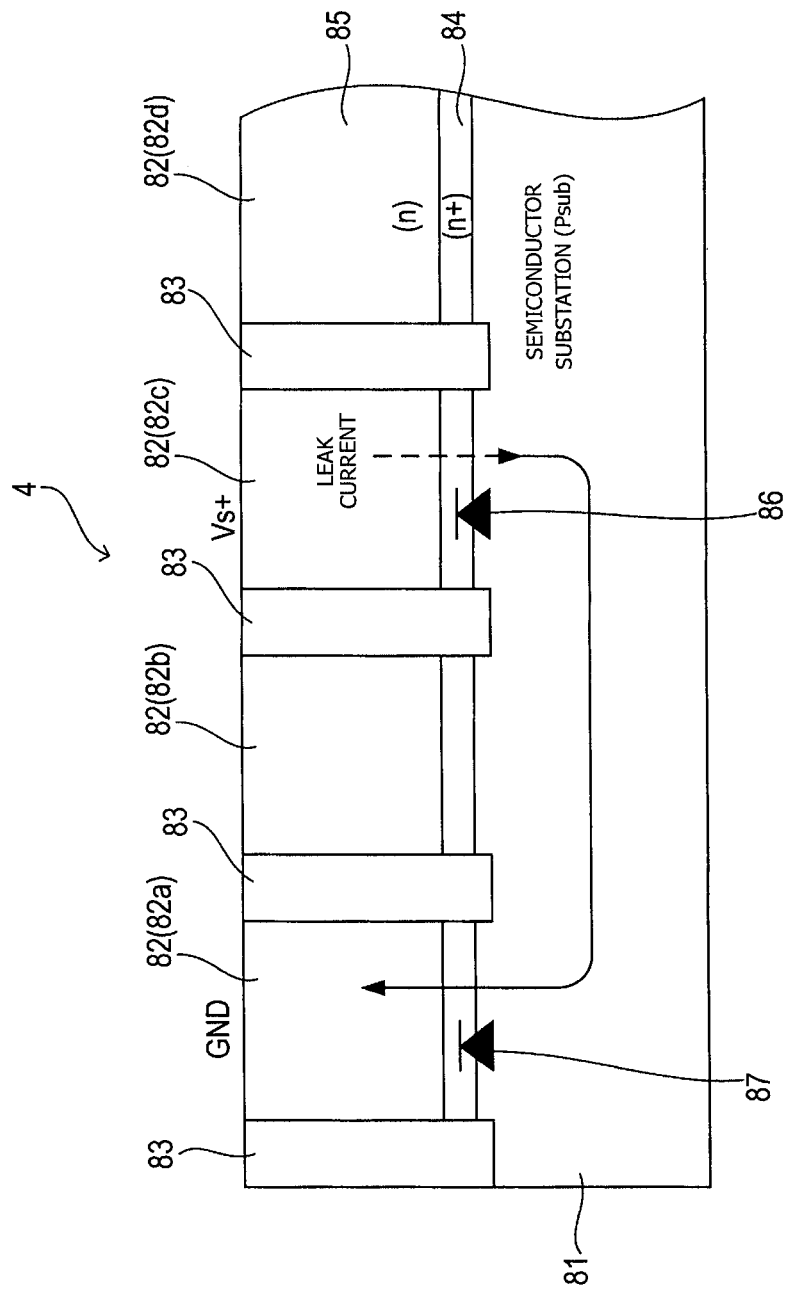
FIG. 4 is a view for describing a path of leak current.

As shown in FIG. 4, the sensor control apparatus 4 is constituted by forming a plurality of semiconductor elements 82 on a semiconductor substrate 81. The semiconductor elements 82 are electrically insulated from one another by an oxide film 83 formed on the semiconductor substrate 81. FIG. 4 shows four semiconductor elements 82a, 82b, 82c, and 82d. The semiconductor element 82a is connected to the ground potential. The ground potential applied to the semiconductor element 82a corresponds to the reference potential set in the sensor control apparatus 4. The semiconductor element 82c is electrically connected to the Vs+ terminal.

The semiconductor substrate 81 is a p-type silicon substrate. An n+ layer 84 is formed on the semiconductor substrate 81, and an n layer 85 is formed on the n+ layer 84. The n+ layer 84 and the n layer 85 are layers into which ions of an n-type impurity are implanted. The n+ layer 84 is higher than the n layer 85 in terms of concentration of the n-type impurity.

Parasitic diodes are formed at the junction surface between the p-type semiconductor substrate 81 and the n+ layer 84. The parasitic diodes 86 and 87 shown in FIG. 4 respectively correspond to the parasitic diodes D25 and D26 shown in FIG. 3.

The sensor control apparatus 4 configured as described above controls the gas sensor 3 which detects the concentration of oxygen contained in exhaust gas.

The gas sensor 3 includes the oxygen concentration detection cell 13 and the oxygen pump cell 11. The oxygen concentration detection cell 13 includes the oxygen-ion conductive solid electrolyte member 25 and the paired detection electrodes 26 and 27 formed on the oxygen-ion conductive solid electrolyte member 25 and generates electromotive force between the paired detection electrodes 26 and 27 in accordance with the oxygen concentration difference therebetween. The oxygen pump cell 11 includes the oxygen-ion conductive solid electrolyte member 21 and the paired pump electrodes 22 and 23 formed on the oxygen-ion conductive solid electrolyte member 21 and pumps oxygen between the paired pump electrodes 22 and 23.

The sensor control apparatus 4 includes the sensor element drive circuit 41, the anomaly detection circuit 44, the control section 45, the logical operation circuit 46, and the negative charge pump 47.

The sensor element drive circuit 41 is a circuit which includes the plurality of semiconductor elements 82 formed on the semiconductor substrate 81 for realizing a current control function and a switching function.

The current control function is a function of controlling the current flowing between the paired pump electrodes 22 and 23 such that the potential difference between the paired detection electrodes 26 and 27 assumes a constant value.

The switching function is a function for switching between a connected state in which the paired detection electrodes 26 and 27 and the paired pump electrodes 22 and 23 are electrically connected to the sensor control apparatus 4 and a cut-off state in which the electrical continuity between the sensor control apparatus 4 and the paired detection electrodes 26 and 27 and the electrical continuity between the sensor control apparatus 4 and the paired pump electrodes 22 and 23 are cut off.

The anomaly detection circuit 44 determines, on the basis of an anomaly determination condition set in advance, whether or not one of the plurality of terminals (i.e., the Ip+ terminal, the COM terminal, and the Vs+ terminal) for connecting the sensor element drive circuit 41 to the paired detection electrodes 26 and 27 and the paired pump electrodes 22 and 23 of the gas sensor 3 has an anomalous potential. In the present embodiment, the anomaly determination condition is that the terminal voltage falls outside a normal voltage range.

In the case where the anomaly detection circuit 44 determines that one of the Ip+ terminal, the COM terminal, and the Vs+ terminal has an anomalous potential, the AND circuits 75, 76, and 77 of the logical operation circuit 46 cause the sensor element drive circuit 41 to perform switching from the connected state to the cut-off state.

In the case where the anomaly detection circuit 44 determines that one of the Ip+ terminal, the COM terminal, and the Vs+ terminal has an anomalous potential, the clock circuit 74 and the AND circuit 78 of the logical operation circuit 46 and the negative charge pump 47 connect the semiconductor substrate 81 to a negative voltage of −3 V which is lower than the ground potential applied to the sensor element drive circuit 41.

In the sensor control apparatus 4 configured as described above, the parasitic diodes D21 to D26 are formed between the semiconductor substrate 81 and the semiconductor elements 82 formed on the semiconductor substrate 81. The parasitic diodes D21 to D26 have characteristics of limiting the current flowing from the semiconductor elements 82 to the semiconductor substrate 81. The parasitic diodes D21 to D26 also have characteristics of allowing the current flowing from the semiconductor substrate 81 to the semiconductor elements 82 to flow more easily as compared with the current flowing from the semiconductor elements 82 to the semiconductor substrate 81.

In the sensor control apparatus 4, leak currents flow from the semiconductor elements 82 to the semiconductor substrate 81 through the parasitic diodes D21, D23, and D25. The magnitudes of the leak currents increase as the temperature of the sensor element drive circuit 41 increases. If the leak current from one semiconductor element 82 reaches the semiconductor substrate 81 through the parasitic diode D21, D23, or D25, the leak current flows toward a semiconductor element 82 whose potential is set to the ground potential (i.e., the semiconductor element 82a) among the plurality of semiconductor elements 82.

Therefore, in the case where there exists a path of leak current which extends from one of the Vs+ terminal, the COM terminal, and the Ip+ terminal, passes through the corresponding semiconductor element 82, reaches the semiconductor substrate 81, and extends from the semiconductor substrate 81 toward another semiconductor element 82 whose potential is the reference potential, a current corresponding to the magnitude of the leak current flows to the gas sensor 3 even in the above-described cut-off state.

In views of this, in the case where one of the Ip+ terminal, the COM terminal, and the Vs+ terminal has an anomalous potential, the sensor control apparatus 4 connects the semiconductor substrate 81 to −3 V which is lower than the reference potential applied to the sensor element drive circuit 41.

Therefore, even when a leak current from a certain semiconductor element 82 reaches the semiconductor substrate 81 through the parasitic diode D21, D23, or D25, the sensor control apparatus 4 can prevent the leak current from further flowing from the semiconductor substrate 81 toward another semiconductor element 82 whose potential is the reference potential.

Thus, the sensor control apparatus 4 can prevent a current corresponding to the magnitude of the leak current from flowing into the gas sensor 3, which flow would otherwise occur even in the above-described cut-off state. As a result, the sensor control apparatus 4 can prevent breakage of the gas sensor 3.

Further, even when a wiring line anomaly (in which at lest one of the wiring lines electrically connected to the gas sensor 3 is shorted to the power supply potential or the ground potential) has occurred, the sensor control apparatus 4 can prevent breakage of the gas sensor 3 by switching to the above-mentioned cut-off state, thereby increasing the possibility that the control system 1 can be restored by exchanging wiring lines.

Further, the sensor control apparatus 4 includes the negative charge pump 47, and when the anomaly detection circuit 44 determines that one of the Ip+ terminal, the COM terminal, and the Vs+ terminal has an anomalous potential, the sensor control apparatus 4 activates the negative charge pump 47 so as to connect the semiconductor substrate 81 to a negative voltage.

Since the sensor control apparatus 4 applies a negative voltage to the semiconductor substrate 81 as described above, the reference potential applied to the sensor element drive circuit 41 can be made equal to or higher than 0 V. In general, the reference potential of the sensor element drive circuit 41 is 0 V. Therefore, the sensor control apparatus 4 can prevent breakage of the gas sensor 3 without changing the reference potential applied to the sensor element drive circuit 41.

Notably, since the negative charge pump 47 is activated in the above-descried cut-off state, noise generated as a result of switching of the negative charge pump 47 does not affect the concentration detection accuracy of the sensor control apparatus 4.

The gas sensor 3 is configured such that when the constant current Icp flows between the paired detection electrodes 26 and 27 of the oxygen concentration detection cell 13, the oxygen concentration around the detection electrode 27 becomes constant.

The sensor control apparatus 4 configured as described above can prevent a current corresponding to the magnitude of the leak current from flowing into the oxygen concentration detection cell 13, which flow would otherwise occur even in the above-described cut-off state. As a result, the sensor control apparatus 4 can prevent blackening of the oxygen concentration detection cell 13.

Notably, the oxygen concentration detection cell 13 corresponds to the electromotive force cell appearing in CLAIMS; the oxygen pump cell 11 corresponds to the pump cell appearing in CLAIMS; the oxygen-ion conductive solid electrolyte member 25 corresponds to the first solid electrolyte member appearing in CLAIMS; the detection electrodes 26 and 27 correspond to the first electrodes appearing in CLAIMS; the oxygen-ion conductive solid electrolyte member 21 corresponds to the second solid electrolyte member appearing in CLAIMS; and the pump electrodes 22 and 23 correspond to the second electrodes appearing in CLAIMS.

The sensor element drive circuit 41 corresponds to the control circuit appearing in CLAIMS; the Vs+ terminal, the COM terminal, and the Ip+ terminal correspond to the connection points appearing in CLAIMS; the anomaly detection circuit 44 corresponds to the anomaly determination section appearing in CLAIMS; the AND circuits 75, 76, and 77 of the logical operation circuit 46 correspond to the state switching section appearing in CLAIMS; and the clock circuit 74 and the AND circuit 78 of the logical operation circuit 46 and the negative charge pump 47 correspond to the potential connection section appearing in CLAIMS.

Exhaust gas corresponds to the gas under measurement appearing in CLAIMS; oxygen corresponds to the particular gas appearing in CLAIMS; and the negative voltage generated by the negative charge pump 47 corresponds to the anomaly-time potential appearing in CLAIMS.

One embodiment of the present disclosure has been described above, but the present disclosure is not limited to the above embodiment and can be embodied in various other forms.

For example, in the above-described embodiment, a full-range air-fuel ratio sensor for detecting the concentration of oxygen in exhaust gas has been described as a gas sensor for detecting the concentration of a particular gas contained in a gas under measurement. However, the gas sensor which is controlled by the sensor control apparatus of the present disclosure is not limited to the full-range air-fuel ratio sensor. No limitation is imposed on the gas sensor controlled by the sensor control apparatus of the present disclosure so long as the gas sensor includes an electromotive force cell and a pump cell. Examples of such a gas sensor include an NOx sensor, etc.

In the above-described embodiment, the reference potential applied to the sensor element drive circuit 41 is the ground potential, and the negative charge pump 47 generates a negative voltage. However, the reference potential applied to the sensor element drive circuit 41 is not limited to the ground potential, and may be a positive voltage or a negative voltage. However, the voltage applied to the semiconductor substrate 81 when the anomaly detection circuit 44 determines that one of the Ip+ terminal, the COM terminal, and the Vs+ terminal has an anomalous potential must be set to be lower than the reference potential.

The function of one component in the above embodiment may be distributed to a plurality of components, or the functions of a plurality of components may be realized by one component. Part of the configurations of the above embodiments may be omitted. At least part of the configuration of each of the above embodiments may be added to or partially replace the configurations of other embodiments. All modes included in the technical idea specified by the wording of the claims are embodiments of the present disclosure.

The present disclosure may be realized in various forms other than the above-described sensor control apparatus 4. For example, the present disclosure may be realized as a system including the sensor control apparatus 4 as a constituent element, a program for causing a computer to function as the sensor control apparatus 4, a non-transitory tangible recording medium, e.g., a semiconductor memory, in which the program is recorded, and a sensor control method.

DESCRIPTION OF REFERENCE NUMERALS

3: gas sensor; 4: sensor control apparatus; 10: sensor element; 11: oxygen pump cell; 13: oxygen concentration detection cell; 21, 25: oxygen-ion conductive solid electrolyte member; 22, 23: pump electrode; 26, 27: detection electrode; 41: sensor element drive circuit; 44: anomaly detection circuit; 45: control section; 46: logical operation circuit; 47: negative charge pump; 74: clock circuit; 75, 76, 77, 78: AND circuit; 81: semiconductor substrate; 82: semiconductor element

The invention claimed is:

1. A control system comprising:
a gas sensor for detecting a concentration of a particular gas contained in a target gas; and
a sensor control apparatus which controls the gas sensor, wherein
the gas sensor includes an electromotive force cell and a pump cell, the electromotive force cell having a first solid electrolyte member and paired first electrodes formed on the first solid electrolyte member and being configured to generate electromotive force between the paired first electrodes in accordance with a difference in concentration of the particular gas therebetween, the pump cell having a second solid electrolyte member and paired second electrodes formed on the second solid electrolyte member and being configured to pump the particular gas between the paired second electrodes, and
the sensor control apparatus includes:
a control circuit having a plurality of semiconductor elements formed on a semiconductor substrate, the semiconductor elements being provided for controlling current that flows between the paired second electrodes such that a constant potential difference is produced between the paired first electrodes, and for switching between a connected state in which the paired first electrodes and the paired second electrodes are electrically connected to the sensor control apparatus and a cut-off state in which electrical continuity between the sensor control apparatus and the paired first electrodes and electrical continuity between the sensor control apparatus and the paired second electrodes are cut off; an anomaly determination section which determines, on the basis of an anomaly determination condition set in advance, whether or not at least one of a plurality of connection points for connecting the control circuit to the paired first electrodes and the paired second electrodes of the gas sensor has an anomalous potential; a state switching section which causes the control circuit to switch from the connected state to the cut-off state, when the anomaly determination section determines that the at least one connection point has an anomalous potential; and a potential connection section which connects the semiconductor substrate to an anomaly-time potential lower than a reference potential applied to the control circuit, when the anomaly determination section determines that the at least one connection point has an anomalous potential.

2. The control system according to claim 1, wherein
the potential connection section includes a negative charge pump for generating a negative voltage, and
when the anomaly determination section determines that the at least one connection point has an anomalous potential, the potential connection section activates the negative charge pump and uses the negative voltage generated by the negative charge pump as the anomaly-time potential.

3. The control system according to claim 2, wherein the gas sensor is configured such that when constant current flows between the paired first electrodes of the electromotive force cell, the concentration of oxygen around one of the paired first electrodes becomes constant.

4. The control system according to claim 1, wherein the gas sensor is configured such that when constant current flows between the paired first electrodes of the electromotive force cell, the concentration of oxygen around one of the paired first electrodes becomes constant.

5. The control system according to claim 1, wherein the reference potential is a ground potential.

6. The control system according to claim 1, wherein the anomaly-time potential is—3 voltage.

7. The control system according to claim 1, wherein
a plurality of parasitic diodes are formed on the semiconductor substrate, and
the plurality of parasitic diodes have cathodes that are connected to the plurality of connection points and anodes that are connected to output terminals of the potential connection section.

* * * * *